United States Patent [19]
Eisenthal

[11] Patent Number: 6,055,051
[45] Date of Patent: *Apr. 25, 2000

[54] METHOD FOR DETERMINING SURFACE PROPERTIES OF MICROPARTICLES

[75] Inventor: Kenneth B. Eisenthal, Ridgewood, N.J.

[73] Assignee: The Trustees of Columbia University in the City of New York, New York, N.Y.

[*] Notice: This patent issued on a continued prosecution application filed under 37 CFR 1.53(d), and is subject to the twenty year patent term provisions of 35 U.S.C. 154(a)(2).

[21] Appl. No.: 09/066,280

[22] Filed: Apr. 24, 1998

Related U.S. Application Data

[63] Continuation-in-part of application No. 08/690,688, Jul. 31, 1996, abandoned.

[51] Int. Cl.[7] ............................................... G02B 1/02
[52] U.S. Cl. ........................................................ 356/318
[58] Field of Search ..................................... 356/317, 318

[56] References Cited

U.S. PATENT DOCUMENTS

| | | | |
|---|---|---|---|
| 4,448,485 | 5/1984 | Bergman et al. | 359/328 |
| 5,348,687 | 9/1994 | Beck et al. | 252/582 |
| 5,552,086 | 9/1996 | Siiman et al. | 252/408.1 |

*Primary Examiner*—Richard A. Rosenberger
*Attorney, Agent, or Firm*—Baker Botts LLP

[57] ABSTRACT

Second harmonic generation (SHG), sum frequency generation (SFG) and difference frequency generation (DFG) can be used for surface analysis or characterization of microparticles having a non-metallic surface feature. The microparticles can be centrosymmetric or such that non-metallic molecules of interest are centrosymmetrically distributed inside and outside the microparticles but not at the surface of the microparticles where the asymmetry aligns the molecules. The signal is quadratic in incident laser intensity or proportional to the product of two incident laser intensities for SFG, it is sharply peaked at the second harmonic wavelength, quadratic in the density of molecules adsorbed onto the microparticle surface, and linear in microparticles density. In medical or pharmacological applications, molecules of interest may be of drugs or toxins, for example.

21 Claims, 5 Drawing Sheets

METHOD FOR DETERMINING SURFACE PROPERTIES OF MICROPARTICLES

This is a continuation-in part application of patent application Ser. No. 08/690,688 filed Jul. 31, 1996, now abandoned.

The United States Government has certain rights in this invention under Awards No. CHE-93-13778 by the National Science Foundation and No. DE FG02 91ER14226 A006 by the Department of Energy.

BACKGROUND OF THE INVENTION

The invention is concerned with analytical methods for determining surface and interface properties.

Surface and interfacial phenomena at the junction between dissimilar media have been of longstanding interest, e.g., in metallurgy, soil engineering and agronomy, energy conversion, medicine, and the electronics industry. Increasingly also, such phenomena are receiving attention in other fields including biological and environmental studies, for example.

For the selective probing of surface properties, the use of nonlinear optical processes such as second harmonic generation (SHG), sum frequency generation (SFG) and difference frequency generation (DFG) has been found to have advantages over other methods, e.g., as based on observing fluorescence. In particular, as compared with the latter, methods based on nonlinear optical processes do not require the introduction of an extraneous agent for light emission at the surface to be studied. Advantageously further, the SHG and SFG methods can be used to study buried interfaces such as liquid-liquid, liquid-solid and solidsolid interfaces, whereas other surface techniques can be used only for vacuum-solid interfaces. The SHG and SFG methods are highly surface specific, and they can be used to study surface dynamic processes with sub-picosecond time resolution as well as static processes.

In most cases, SHG and SFG experiments are performed on planar surfaces. This has restricted the range of systems studied.

SUMMARY OF THE INVENTION

A nonlinear coherent process can be used for the detection of a non-metallic adsorbate on centrosymmetric microparticles in centrosymmetric bulk media, or, even if the microparticles are not centrosymmetric, of non-metallic molecules of interest at the surface of the microparticles where such molecules are centrosymmetrically distributed inside and outside the microparticles but not at the surface of the microparticles. Such a system is irradiated with fundamental light having a first wavelength, and second harmonic (SH) coherent light is observed which is generated at the surface of the microparticles. Analogously, sum frequency (SF) or difference frequency (DF) coherent light can be generated on irradiation by means of two light beams. Such generation can be detected also in the absence of an adsorbate when the microparticles have a net surface charge.

The method can be used to investigate the surfaces of liquid or solid microparticles in liquids or gases, e.g., aerosols, colloids, sols, vesicles, liposomes, emulsions, and of solid-state and polymer beads. Such investigations are of interest in diverse fields including drug delivery, crude oil mining and recovery, soil analysis (where pollutants and bacteria are typically found at the interface between micron-size clay particles and water), and the manufacture of solar cells using a semiconductor microparticle colloid.

DETAILED DESCRIPTION OF EXEMPLARY EMBODIMENTS

As used herein, the term light designates suitable electromagnetic radiation which is not limited to visible light. Optical wavelengths of particular interest range from the far ultraviolet to the deep infrared. For certain studies, soft X-rays and synchrotron radiation may be advantageous.

Figure 1:
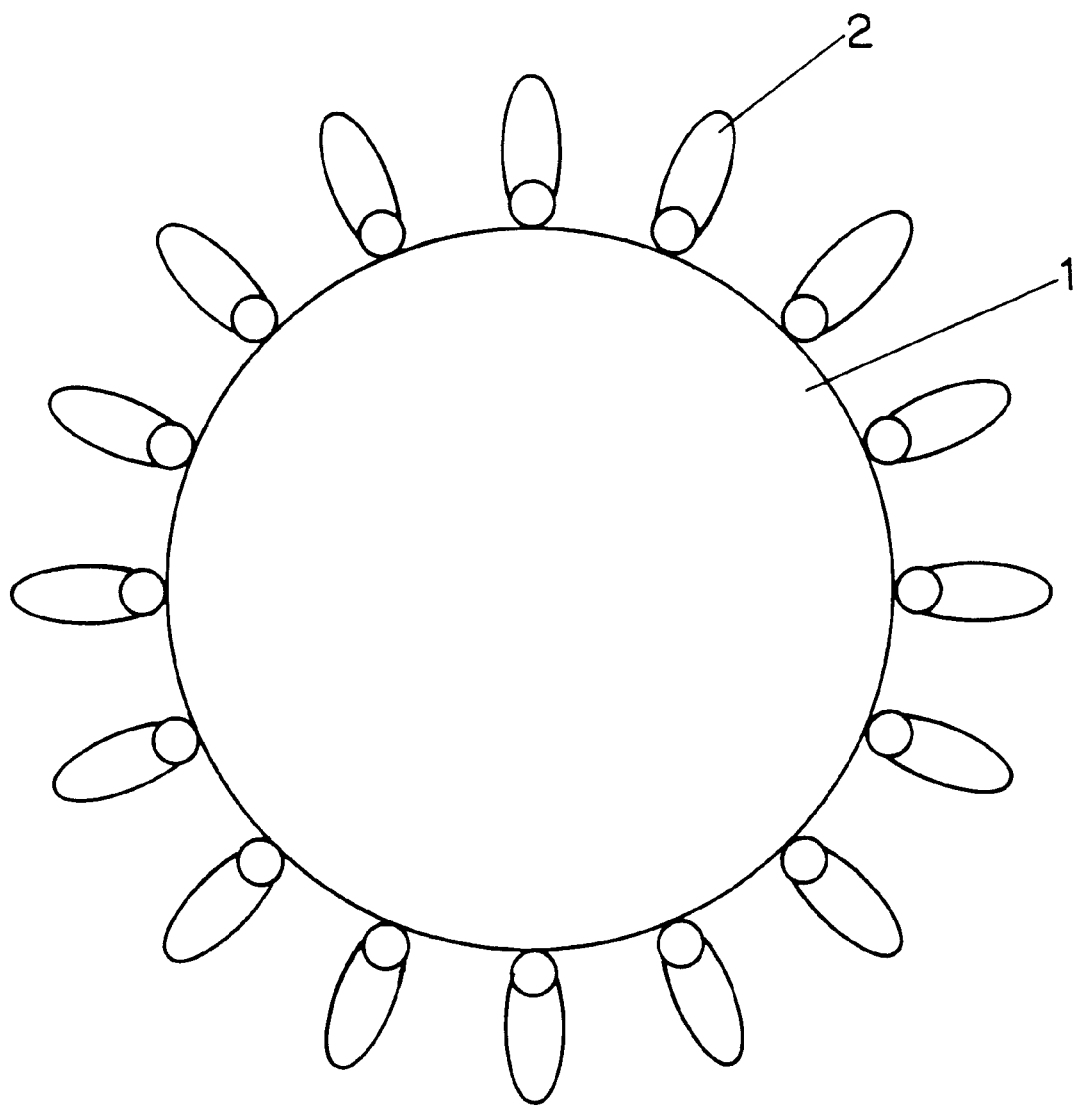
FIG. 1 is a cross section, greatly enlarged, of a centrosymmetric microparticle, here a microsphere, having adsorbed molecules.

FIG. 1 shows a centrosymmetric microparticle 1 and adsorbed molecules 2. The microparticle shown is spherical, with ellipsoids, cubes and octahedra being other examples of centrosymmetric particle shapes. Of its own, the centrosymmetric microparticle does not give rise to SHG or SFG. But, on account, e.g., of size, orientation or polarizability of adsorbed molecules, the adsorbate will yet lead to SHG and SFG. The adsorbate is non-metallic, with electrical conductivity in the range from insulators through semiconductors.

SHG/SFG can be detected also in the absence of adsorbed molecules when the microparticle has a net surface charge, as is the case for polystyrenesulfate, for example. The electrostatic field of the surface charges generates a SH or SF signal due to its polarization of the bulk water molecules.

In FIGS. 2–5, dots correspond to measured values and the solid lines represent theoretical comparison functions. These figures relate to specific experiments carried out with a Ti:sapphire light source at a wavelength of 854 nanometers. Lasers at other wavelengths can be used, and the SHG and SFG methods can be used in the field as well as in laboratory environments.

In the experiments, the Ti:sapphire oscillator provided 100-femtosecond pulses of fundamental light having a wavelength of 854 nanometers, at a repetition rate of 82 MHZ. This light was focused into a 0.2-cm-long sample cell. Second harmonic photons were detected in the transmitted direction using single photon counting. Filters and a monochromator were used to separate the SH photons from the fundamental and any background signals as may be due to fluorescence or Raman scattering, for example. The detected signals were normalized to solution turbidity at $\omega$ and $2\omega$, when either the solute or microparticle concentration was varied.

The microparticles used in the experiments were polystyrene (latex) microspheres obtained from the Polysciences company. These microparticles have a negative surface charge due to the presence of sulfate ($-SO_4^-$) groups. There are approximately $10^7$ charges per microparticle. The microparticles are uniformly spherical and are supplied as monodisperse aqueous solutions. Particle diameter is 1.05±0.03 micrometer.

The samples were prepared using doubly distilled water. The solution pH in all experiments was 6.5±0.2. Ionic strength was adjusted using KCl. Malachite green chloride obtained from the Aldrich company was checked for purity using high-pressure liquid chromatography (HPLC). All measurements were performed at 22° C.

Second harmonic generation was only observed from bulk solutions containing microspheres. Water alone showed no detectable signal. Bulk samples of aqueous malachite green ($<10^{-3}$ M) showed a two-photon excited fluorescence signal with a small tail extending to the second harmonic wavelength of 427 nm. The fluorescence is an unrelaxed emission, centered at 460 nm, from an excited ($S_2$) state to the ground state ($S_0$). On addition of polystyrene microspheres to the malachite green solution, an intense second harmonic signal at 427 nm was observed. The signal was a factor of 1000 greater than that observed from solutions of microspheres without malachite green, and a factor of 300 greater than bulk solutions of malachite green alone.

Figure 2:
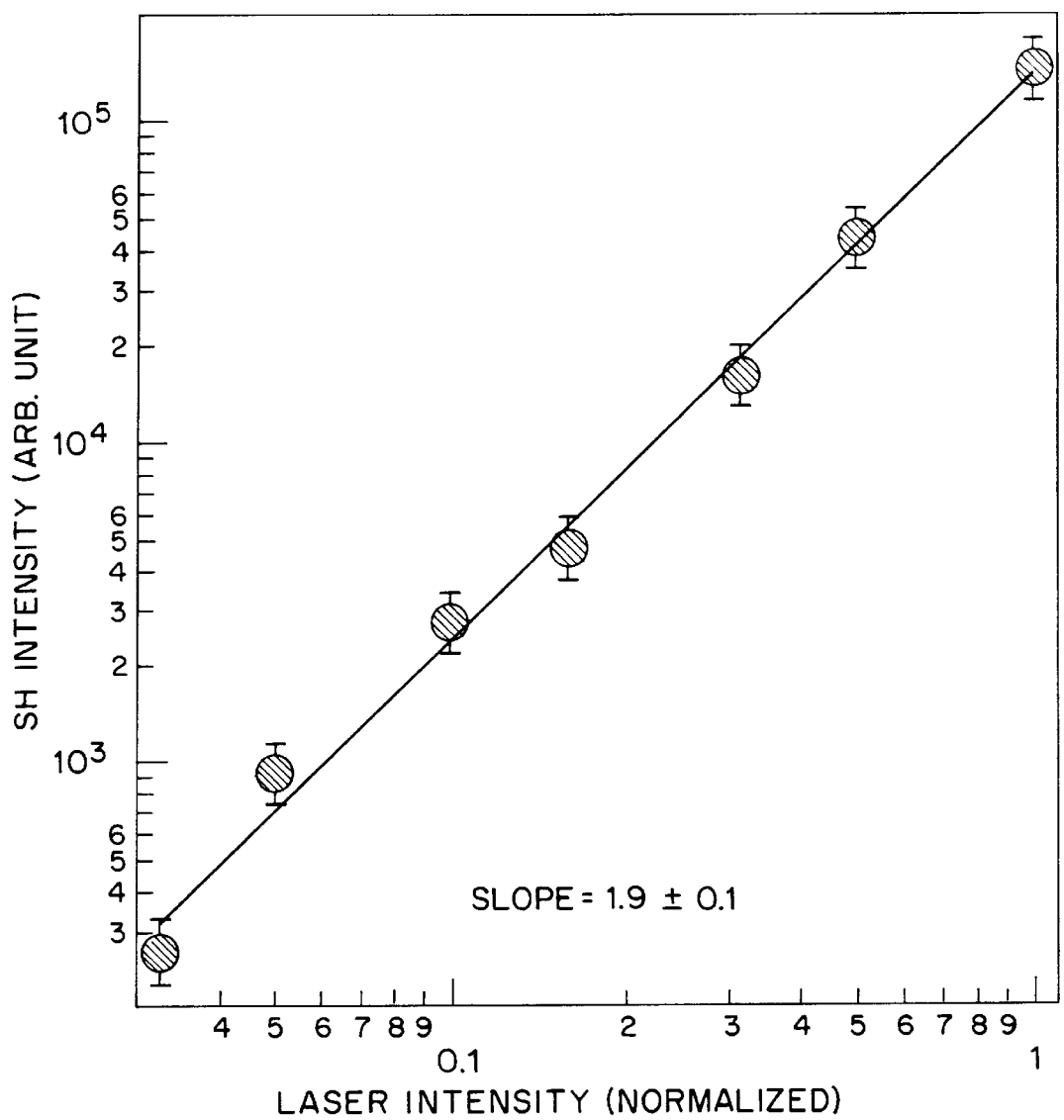
FIG. 2 is a graph of second harmonic intensity as a function of incident laser intensity in an experiment.

A number of experiments were performed to establish that the observed signal is indeed second harmonic, that it originates from the surface of the microparticles, and that it is not due to a nonlinear bulk process. The spectrum of the signal was examined and found to be sharply peaked at $2\omega$ (427 nm). A small two-photon fluorescence signal, centered at 460 nm was observed from malachite green samples. The monochromator effectively reduces the signal from two-photon fluorescence to less than $\frac{1}{200}$ of the SH signal. By varying the focus of the input laser and using cells having path lengths of 2 mm and 1 cm, respectively, it was shown that the second harmonic did not originate from either the input or output surfaces of the cell. Furthermore, the signal from all samples displaying SHG showed quadratic dependence on the incident fundamental intensity, confirming SH origin. This is illustrated by FIG. 2 which shows SH intensity from a bulk aqueous solution of 1.05-micrometer polystyrenesulfate microspheres with malachite green (5 micromole).

To demonstrate that the SH signal originates from the surface of the microparticles, the adsorption isotherm which gives the surface population of malachite green on the microparticle as a function of bulk malachite green concentration, was measured. The SH signal should vary quadratically with the adsorbate density on the microsphere as it does for planar surfaces. Using the adsorption isotherm to obtain the interface population, it was shown that the SH signal from the microparticle solutions obeyed quadratic dependence on the density of malachite green adsorbed on the microparticle surfaces.

Figure 3:
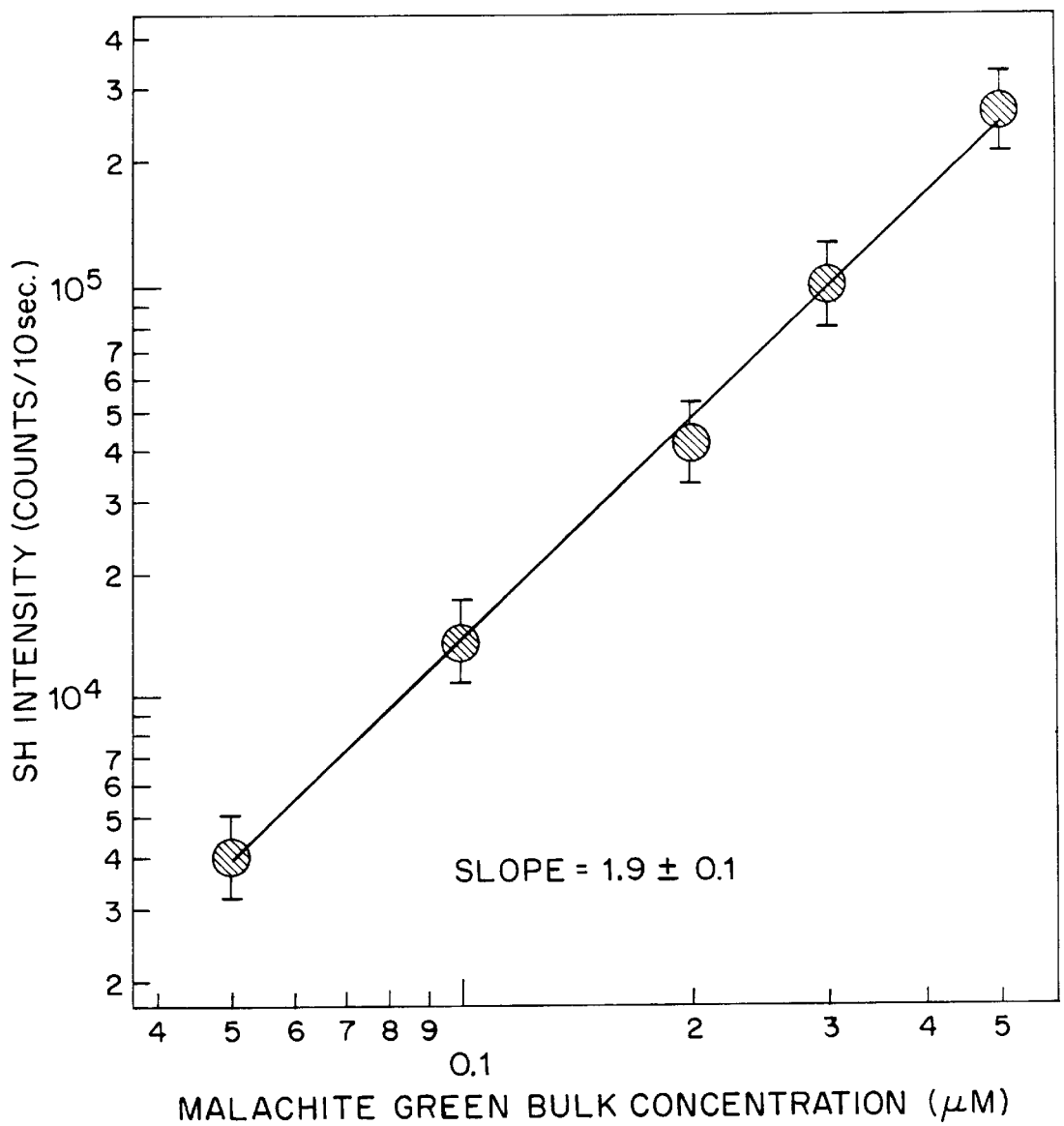
FIG. 3 is a graph of second harmonic intensity as a function of bulk malachite green concentration in test solutions.

This is illustrated by FIG. 3 which shows SH signal intensity as a function of bulk malachite green density at a constant density of 8.25 times $10^8$ microspheres/cm$^3$ for 1.05-micrometer polystyrenesulfate microspheres. The data shown is for the linear region of the adsorption isotherm where the density of malachite green is linearly related to bulk concentration.

This is further evidence that the observed SH signal arises from the surfaces of the microparticles, and rules out hyper-Rayleigh scattering as the latter would scale linearly with the number density of the malachite green. The more than three-hundred-fold enhancement of the SH signal which was observed when the microspheres were added to the malachite green solution, indicates that it is the species adsorbed at the microparticle surfaces that are primarily responsible for the observed SHG.

Figure 4:
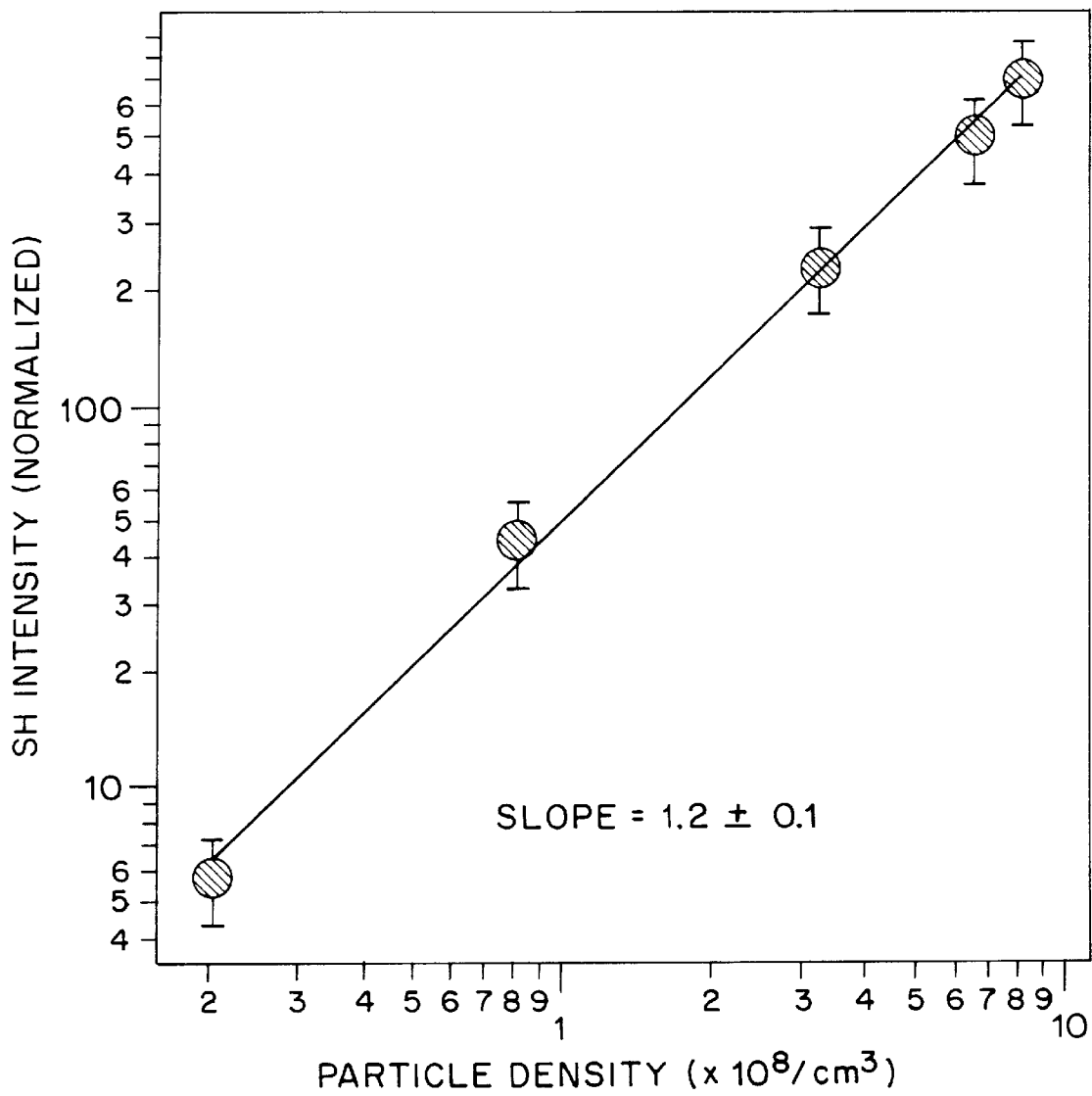
FIG. 4 is a graph of second harmonic intensity as a function of microparticle density in test solutions.

In order to probe the coherent nature of the process, the dependence of the second harmonic generation on the density of microspheres in solution was investigated. FIG. 4 shows the results for solutions of malachite green at a fixed concentration of 5 micromole that contain 1.05-micrometer microspheres over a range of 0.21 to 8.25 times $10^8$ microspheres/cm$^3$. At these microparticle densities, the average inter-particle distance ranges from 36 to 11 micrometers. The bulk solution concentration of malachite green was sufficient to saturate the microparticle surfaces. The observed linear dependence indicates that the microparticles do not interact coherently. If the microparticles were interacting coherently, a nonlinear dependence of the SH signal on the microparticle density would result.

Figure 5:
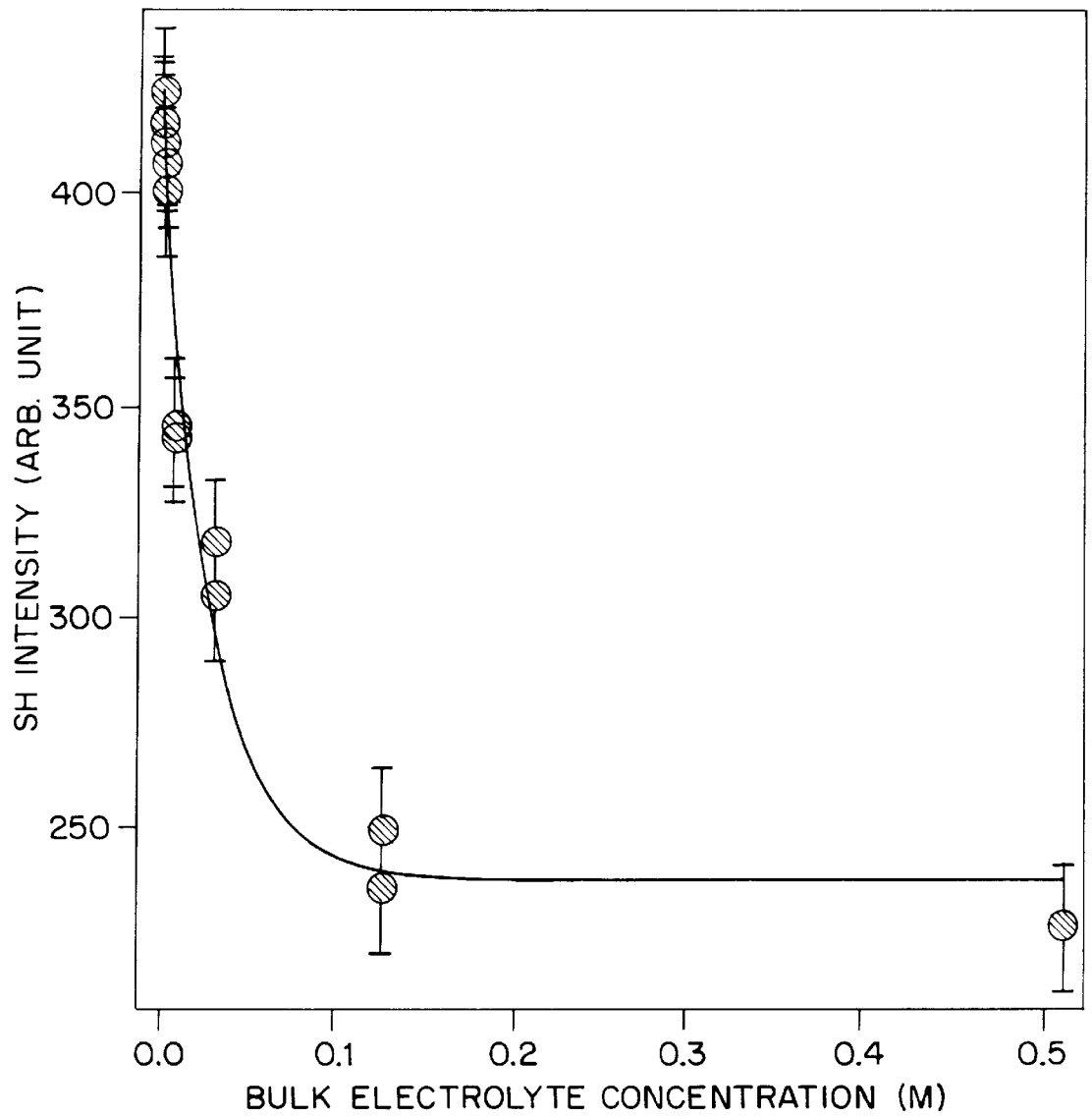
FIG. 5 is a graph of second harmonic intensity as a function of ionic strength in test solutions.

Second harmonic generation from an interface can also result from action of a static electric field on the bulk solution due to surface charges. This field is responsible for a $\chi^{(3)}$-contribution to the SHG due to the polarization of solvent species by the surface field, in addition to a $\chi^{(2)}$-contribution. Such a $\chi^{(3)}$-contribution is known at silica-water and charged monolayer-water interfaces, with the contribution to the total SH polarization varying with the electrolyte concentration or ionic strength. In the presence of a significant $\chi^{(3)}$-contribution, increasing the electrolyte concentration at constant surface charge density should reduce the penetration of the static electric field into the bulk water, thereby reducing the polarization of the water molecules and hence the $\chi^{(3)}$-contribution to the signal. This has indeed been observed for bulk solutions of 1.05-micrometer particles alone, as illustrated by FIG. 5. But no such dependence of signal on electrolyte concentration was observed for microparticle solutions containing malachite. Thus, the $\chi^{(3)}$-contribution is not significant relative to the $\chi^{(2)}$-contribution of malachite green adsorbed on the microparticle surface.

As the magnitude of the SH effect depends on many parameters, of which some typically may not be known, the interpretation of coherent SH radiation in accordance with the invention usually is with reference to calibration and comparison data. If microparticle size is less than about one-twentieth of the sensed wavelength, analytical results may not be satisfactory for this reason alone.

For microparticle surface analysis per se, the mean distance between centrosymmetric microparticles is preferably greater than the coherence length of the probe radiation. Otherwise, with increased microparticle density, the SH/SF signal becomes nonlinearly dependent on microparticle density. This effect, too, may be used for analytical purposes.

More specifically with respect to the SFG method, if one light beam wavelength is in the infrared range, the method is sensitive to the vibration of adsorbed molecules. This leads to increased analytical sensitivity as the vibration spectrum can be obtained and used for identification of adsorbates and the characterization of the environment of the adsorbate.

Methods of the invention can be used as analytical tools in electronics, energy conversion, soil engineering and agronomy, biological/environmental studies, medicine and pharmacology, for example. The surface being investigated may be that of a microsome, i.e. a liposome structure formed from the membrane of a cell, or a liposome for drug delivery or similar release and capture properties, or a biological cell where the substance of interest such as a drug or toxin present at the surface of the cell(e. g. the cell membrane) is detected. Molecules in the bulk plasma inside the cell or outside the cell will not contribute to the second harmonic, sum frequency or difference frequency signal because molecules in bulk liquids are randomly oriented, whereas at the cell surface the asymmetry aligns the molecules. Thus, such methods provide for an analytical tool for ascertaining whether or not the substance will adhere to cells, liposomes, emulsions and similar structures. These methods can be used to determine release and penetration times by the time dependent change in the signal when the substance of interest is mixed with the liposome.

In pharmacology, methods of the invention may also be used in the development of combinatorial libraries, obviating prior-art use of fluorescent tags.

I claim:

1. A method for detecting a non-metallic surface feature on microparticles, comprising:

irradiating the microparticles having the surface feature with at least one beam of fundamental light, with either (i) the microparticles being centrosymmetric or (ii) the surface feature comprising non-metallic molecules which are not centrosymmetrically distributed, and the microparticles having an interior and an exterior in which such molecules are centrosymmetrically distributed; and sensing coherent light which has been nonlinearly generated upon second-order interaction of the fundamental light with the surface feature.

2. The method according to claim 1, wherein a single beam is used for irradiating, and wherein the sensed coherent light has been generated as second harmonic radiation.

3. The method according to claim 1, wherein two beams are used for irradiating, and wherein the sensed coherent light has been generated as sum/difference frequency radiation.

4. The method according to claim 3, wherein at least one of the beams has a wavelength in the infrared range.

5. The method according to claim 1, wherein the microparticles are in a solution.

6. The method according to claim 1, wherein the microparticles are in a colloidal solution.

7. The method according to claim 1, wherein the microparticles are in an emulsion.

8. The method according to claim 1, wherein the microparticles are in a sol.

9. The method according to claim 1, wherein the microparticles are in an aerosol.

10. The method according to claim 1, wherein the microparticles are in a vesicle.

11. The method according to claim 1, wherein the microparticles are in a liposome.

12. The method according to claim 1, wherein the microparticles are in solid-state beads.

13. The method according to claim 1, wherein the microparticles are polymer beads.

14. The method according to claim 1, wherein the microparticles are in a clay.

15. The method according to claim 1, wherein the surface feature comprises adsorbed molecules.

16. The method according to claim 1, wherein the surface feature comprises an electrical charge distribution.

17. The method according to claim 1, wherein the light being sensed has a wavelength less than approximately 20 times microparticle diameter.

18. The method according to claim 1, wherein the beam has a coherence length less than mean distance between the particles.

19. The method according to claim 1, wherein the microparticles are biological cells.

20. The method according to claim 19, wherein the surface feature comprises a drug.

21. The method according to claim 19, wherein the surface feature comprises a toxin.

* * * * *